United States Patent [19]
Knollmueller

[11] 3,965,135
[45] June 22, 1976

[54] ALKOXYSILANOL CLUSTER COMPOUNDS AND THEIR PREPARATION

[75] Inventor: Karl O. Knollmueller, Hamden, Conn.

[73] Assignee: Olin Corporation, New Haven, Conn.

[22] Filed: Sept. 24, 1975

[21] Appl. No.: 616,439

[52] U.S. Cl. .................. 260/448.8 A; 260/448.8 R; 252/78
[51] Int. Cl.² .................. C07F 7/18; C07F 7/04
[58] Field of Search ............................ 260/448.8 A

[56] References Cited
UNITED STATES PATENTS

| | | | |
|---|---|---|---|
| 2,566,364 | 9/1951 | Pedlow et al. | 260/448.8 A X |
| 2,995,593 | 8/1961 | Kovacich et al. | 260/448.8 A |
| 3,019,191 | 1/1962 | Furby et al. | 260/448.8 A X |

*Primary Examiner*—Paul F. Shaver
*Attorney, Agent, or Firm*—Kenneth P. Glynn

[57] ABSTRACT

Novel alkoxysilanol cluster compounds are described having the formula $RSi[OSi(OR')_3]_2OH$ wherein R is hydrogen, an alkyl, alkenyl, aryl or aralkyl group and each R' is independently selected from the same group as R with the proviso that at least a majority of R' radicals are sterically hindered alkyl groups having at least 3 carbon atoms. The preparation of these novel alkoxysilanol cluster compounds is also described.

15 Claims, No Drawings

ALKOXYSILANOL CLUSTER COMPOUNDS AND THEIR PREPARATION

The present invention is directed to novel oxysilanol compounds and their preparation. More particularly, the present invention is directed to novel alkoxysilanol cluster compounds, and their preparation, the compounds having the general formula:

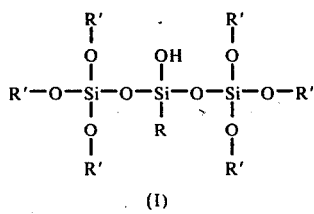

(I)

wherein R is hydrogen, an alkyl, alkenyl, aryl or aralkyl and each R' is independently selected from the same group as R with the proviso that at least a majority of R' radicals are sterically hindered alkyl groups having at least 3 carbon atoms. This general Formula (I) may also be written in an abbreviated form as $RSi[OSi(OR')_3]_2OH$ wherein R and R' are as defined.

Silicate esters, silanes, silanols, oxysilanes and oxysilanols are well known for their utility as functional fluids and many of these compounds have been proposed for use as heat transfer fluids, hydraulic fluids, brake fluids, transmission fluids and the like. Novel alkoxysilanol compounds with desirable functional fluid properties have now been discovered which have heretofore not been described in the literature. The novel compounds of the present invention are alkoxysilanol compounds which are silicon-oxygen balanced cluster compounds of Formula (I) shown above. Morgan et al in the Journal of The American Chemical Society, Vol. 73, pages 5193-5 (1951), described compounds which are believed to be the closest prior art compounds to those of the present invention, but the Morgan et al compounds are centered with a silicon atom completely enclosed by oxygen atoms, unlike the compounds of the present invention.

As mentioned, the compounds of the present invention are those represented by the Formula (I) above wherein R is hydrogen, an alkyl, alkenyl, aryl or aralkyl. Desirably, R is hydrogen, an alkyl or an alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula (I), each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 24 carbon atoms and preferably are sterically hindered alkyl groups having about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered groups include sec. butyl, isobutyl, 2-ethyl butyl, 2-ethyl pentyl, 3-ethyl pentyl, 2-ethyl hexyl, 3-ethyl hexyl, and 2,4-dimethyl-3-pentyl, etc.

In the method of preparing the novel alkoxysilanol cluster compounds of the present invention, a trihalosilane is reacted with a trialkoxysilanol in the presence of a hydrogen halide acceptor base, and optionally, a solvent, to obtain an intermediate compound which is subsequently reacted with water to produce a cluster compound-containing product.

The trihalosilane used in the method of preparing the cluster compounds of the present invention is a substituted trihalosilane of the formula:

wherein R is that which is defined above and X is a halogen selected from F, Cl, Br and I, desirably from Cl, Br and I, especially Cl.

The trihalosilane of Formula (II) above is reacted with a trialkoxysilanol with sterically hindered alkoxy groups and is represented by the formula:

wherein R' is defined above.

The trihalosilane and trialkoxysilanol are reacted in the presence of a hydrogen halide acceptor base compound. The acceptor may be any compound which will accept hydrogen halide and thereby promote the formation of the intermediates and the cluster compounds of the present invention pursuant to the equations shown below. Among the preferred acceptors for this initial reaction are the nitrogenated tertiary organic base compounds having at least 3 carbon atoms, e.g., the lower alkyl and aryl tertiary amines such as triethyl amine, tributyl amine, as well as pyridine, substituted pyridine, N,N'-dimethylaniline, etc.

The reactions which occur during the initial reaction in the formation of the novel cluster compounds of the present invention using the above reactants may be represented by the following equations (A) and (B) as follows:

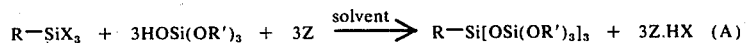

wherein Z is the hydrogen halide acceptor base, and the other reactants are described above, and the product is a useful cluster alkoxysilane compound related to the cluster alkoxysilanols of the present invention;

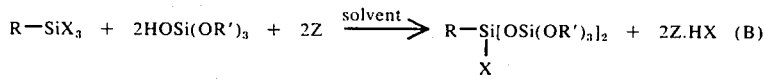

$$R-SiX_3 + 2HOSi(OR')_3 + 2Z \xrightarrow{solvent} R-\underset{X}{\underset{|}{Si}}[OSi(OR')_3]_2 + 2Z.HX \quad (B)$$

wherein R, R', X and Z are defined above, and the product is an intermediate compound useful in the preparation of the cluster alkoxysilanols of the present invention.

The above equations suggest that the principal initial reactions in the method of preparing the cluster compounds of the present invention be carried out in a solvent. While the solvent is not necessary, it does serve to moderate the rate of reaction and thereby to ultimately enhance the separation of the acceptor Z-hydrogen halide HX from the cluster compound product. The solvent used may be any nonprotonic solvent which dissolves the reactants and does not interfere with the Equation (A) reaction. Among the solvents which may be used are benzene, toluene, xylene, high boiling petroleum ether, other ethers such as tetrahydrofurane, and the like.

In reacting the above constituents according to the method of the present invention, in general about 1.5 to about 4 and preferably about 1.8 to about 2.5 moles of the trialkoxysilanol is used per mole of trihalosilane. The hydrogen halide acceptor base is advantageously used in a stoichiometric amount based on the amount of trihalosilane used, e.g., about 2 moles of acceptor per mole of trihalosilane. In general, about 1.5 to about 4 moles, and preferably about 1.8 to about 2.5 moles of the acceptor is used per mole of trihalosilane. The total solvent used in the reaction is a matter of choice and not critical to the reaction, although good results are achieved when about 20 moles to about 80 moles, and preferably about 40 to about 60 moles of solvent is used per mole of trihalosilane. In general, about 0.3 to about 6 parts of solvent per part by weight of total reactants, and preferably about 1 to about 6 parts of solvent per part by weight of total reactants, may be used.

The reactants shown in Equations (A) and (B) above react in a very short period of time and a significant amount of reaction product is obtained in a matter of minutes. Because the reactions occur in most cases in such a short period of time and because the product obtained may be stored in the reaction mixture for long periods of time, there is no criticality to the residence time involved in the reactions. However, for economical commercial production the reactions may be permitted to proceed so that a substantial amount of the above intermediate compound shown in Equation (B) is obtained, e.g., for at least about 20 minutes, before the intermediate compound containing reaction mixture is subjected to hydrolysis. Desirably, the above reactions shown in Equations (A) and (B) are permitted to proceed for at least about ½ hour to about 24 hours or even longer, preferably for about 2 hours to about 12 hours. As mentioned, these ranges are suggested for economic reasons and are not critical to the method.

After the initial reactions are completed to a desirable degree, water is added to the reaction mixture whereby the intermediate compound is converted to an alkoxysilanol cluster compound of the present invention by a condensation reaction according to the following equation:

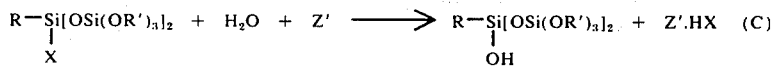

$$R-\underset{X}{\underset{|}{Si}}[OSi(OR')_3]_2 + H_2O + Z' \longrightarrow R-\underset{OH}{\underset{|}{Si}}[OSi(OR')_3]_2 + Z'.HX \quad (C)$$

wherein Z' may be any base defined by Z above, or Z' may be an inorganic acceptor base which is water soluble. When the acceptor base is one which is water soluble a two phase reaction mixture system may advantageously occur due to the excess water. Acceptable inorganic water soluble bases include $NaHCO_3$, $Na_2CO_3$, buffers such as $NaOOCCH_3$, and the like. By using a water soluble acceptor base to carry out the reaction according to Equation (C) wherein the alkoxysilanol cluster compounds of the present invention are obtained, cleavage of some of the OR' groups is avoided both in the organic solvent and the water added thereto. In general, at least about 0.8 moles of water is added and there is no upper limit to the amount of water employed except limitations inherent in commercialization of the method of the present invention. In general, about 0.8 to about 500 moles or even more, and preferably about 1 to about 100 moles of $H_2O$ is used per mole of intermediate compound. The additional acceptor base Z' may be added in an amount of about 0.7 to about 5 moles, and preferably about 0.9 to about 1.5 moles per mole of intermediate compound.

The reactions represented by Equations (A), (B), and (C) may be performed at very low temperatures, room temperature, or even very high temperatures as long as there is no detrimental effect on the reactants or products. Thus, the reaction may be carried out at −30°C up to the reflux temperature of the lowest boiling constituent, but it is preferably carried out at about 0°C to about 100°C. In a preferred batch method embodiment, the reaction is started at a low temperature, e.g., between −10°C and 20°C, to minimize losses of volatile trihalosilanes and is completed at a higher temperature to drive the intermediate compound-producing reaction as far as possible to completion and then the water is added to hydrolyze the intermediate. Of course, a continuous operation may be employed with a series of reactors in which the first reactor is maintained at the lower temperature and each subsequent reactor is incrimentally higher in temperature to drive the intermediate compound-producing reaction to completion. In any event, the cluster compounds are separated from the final product mixture by filtrations, distillations or other conventional separation techniques, and the particular separation system chosen merely depends upon the desired purity of the final product and its ultimate utility.

The novel cluster compounds obtained by the method of the present invention are those represented by Formula (I) above and contain an adequate number of silicon atoms to produce good lubricating properties without the need to add lubricity improvers. Additionally, the silicon atoms are adequately shielded by the significant number of sterically hindered alkyl groups having at least 3 carbon atoms and this assures protection against attack by water. Thus, the novel cluster compounds of the present invention have been found to have good hydrolytic stability, good lubricating properties and low ASTM viscosity indices with many having pour points below $-40°C$. The cluster compounds exhibit these properties both in substantially pure form and in mixture with the alkoxysilane obtained by the reaction set forth in Equation (A) above.

The following examples illustrate various embodiments of the present invention, but the present invention should not be construed to be limited thereto:

EXAMPLE 1

A one liter flask is equipped with a heater, stirrer, reflux condenser, thermometer and equilibrated dropping funnel. To prevent moisture from entering, the reflux condenser is topped with a $CaCl_2$ tube while a slow stream of dry nitrogen is passed through the apparatus via the equilibrated dropping funnel. The flask is charged with 57.85 grams (0.219 moles) of a trialkoxysilanol having the formula $HOSi(OC_4H_9 sec.)_3$, 24 grams (0.303 moles) of pyridine as the acceptor base and 300 ml. of benzene solvent. A solution of 10.9 grams (0.073 moles) of a trihalosilane having the formula $CH_3SiCl_3$ in 90 ml. of benzene is placed into the dropping funnel. The flask contents are set at an initial temperature of 15°C and the trihalosilane solution is added dropwise at such a rate as to maintain the initial temperature of 15°C. After the addition is completed, the contents of the flask are stirred without cooling for about 30 minutes and are then heated to 55°C and maintained at that temperature for about 5 hours. The contents of the flask are then allowed to cool to room temperature and allowed to stand for about 12 hours.

The product mixture obtained is first passed through a filter to remove the pyridine hydrochloride which forms. Next the benzene phase product mixture filtrate is extracted with 200 ml of water so as to hydrolyze any Si-Cl bonds to Si-OH bonds. The extraction is performed four times and after the last wash the water is chloride free. The mixture is then passed over $CaCl_2$ and $MgSO_4$ to remove any water remaining therein, and is then subjected to vacuum stripping.

The filtered, hydrolyzed, dried product (crude weight 58.4 grams) is fed to a micro vigreux stripping column at about 0.05 mm Hg.

The first and second fractions are removed at the 60° to 140°C range and found to contain unreacted trialkoxysilanol and disiloxanes (total weight 11.2 grams)

The third fraction is taken off at about 148° to 150°C and found to be about 9.4 grams of an alkoxysilanol cluster compound of the present invention having the formula $CH_3Si[OSi(OC_4H_9sec.)_3]_2OH$. The generic formula is $C_{35}H_{58}O_9Si_3$. Based on this formula, the calculated component amounts are calculated to be: C—51.24%; H—9.8%; Si—14.38%; found C—52.4%; H—9.74%; Si—14.2%. The —OH radical is confirmed by IR analysis. The theoretical molecular weight is 586 and 590 is found.

The fourth fraction is taken off at about 194° to 196°C and is found to be about 34.5 grams of a cluster compound product having the formula $CH_3Si[OSi(OC_4H_9sec.)_3]_3$. The generic formula is $C_{37}H_{84}O_{12}Si_4$; calculated C—53.31%; H—10.16%; Si—13.48%; found C—53.3%; H—10.1%; Si—13.7%. Calculated molecular weight 834; found 830.

EXAMPLE 2

The procedure of Example 1 is repeated with the following constituents and amounts:
  333.2 grams (1.26 moles) of $HOSi(OC_4H_9sec.)_3$;
  89.7 grams (1.134 moles) of pyridine in 200 ml of benzene;
  41.2 grams (0.252 moles) of $C_2H_5SiCl_3$ in 100 ml of benzene.

The initial reaction is carried out at 4°C followed by heating to 65°C for 12 hours. The recovery and hydrolysis procedure of Example 1 is repeated and a mid-range fraction boiling at about 162°C at 0.025 mm Hg is found to contain 109.5 grams (72.3% yield) of an alkoxysilanol cluster compound of the present invention having the formula $C_2H_5Si[OSi(OC_4H_9sec.)_3]_2OH$. The generic formula is $C_{26}H_{60}O_9Si_3$, calculated C—52.96%; H—10.06%; Si—14.02%; found C—52.58%; H—10.16%; Si—13.56%. Calculated molecular weight 601; found 640.

The high boiling fraction is taken off at 181 to 185°C at 0.03 mm Hg is determined to contain 30.4 grams (14.2% yield) of a cluster compound having the formula $C_2H_5Si[OSi(OC_4H_9sec.)_3]_3$. The generic formula is $C_{38}H_{86}O_{12}Si_4$; calculated C—53.86%; H—10.23%; Si—13.26%; found C—53.33%; H—10.26%; Si—13.50%. Calculated molecular weight 847; found 875.

EXAMPLE 3

The procedure of Example 1 is repeated with the following constituents and amounts:
  92.5 grams (0.35 moles) of $HOSi(OC_4H_9sec.)_3$;
  38.7 grams (0.49 moles) of pyridine in 400 ml of benzene;
  24.67 grams (0.117 moles) of $C_6H_5SiCl_3$ in 100 ml of benzene.

The reaction is initially carried out at 10°C and then completed at 55°C for 12 hours. The recovery and hydrolysis procedure of Example 1 is used and a fraction of product is removed at about 182°C and 0.01 mm Hg and is determined to contain 51.7 grams (68.3% yield) of an alkoxysilanol cluster compound product having the formula $C_6H_5Si[OSi(OC_4H_9sec.)_3]_2OH$. The generic formula is $C_{30}H_{60}O_9Si_3$; calculated C—55.5%; H—9.3%; Si—12.98%; found C—55.48%; H—9.4%; Si—12.9%. Calculated molecular weight 649; found 670.

The distillation residue remaining after the above fraction solidifies and is found to contain 14.35 grams (13.7% yield) of a cluster compound having the formula $C_6H_5Si[OSi(OC_4H_9sec.)_3]_3$. This residue is recrystallized from $CH_3OH$ and has a melting point of about 169°C. The generic formula is $C_{42}H_{86}O_{12}Si_4$; calculated C—56.33%; H—9.68%; Si—12.55%; found C—55.99%; H—9.67%; Si—12.60%. Calculated molecular weight 895; found 895.

EXAMPLE 4

The procedure of Example 1 is repeated with the following constituents and amounts:
  127.5 grams (0.481 moles) of $HOSi(OC_4H_9sec.)_3$;
  63.1 grams (0.797 moles) of pyridine in 600 ml of benzene;

50 grams (0.236 moles) of C₆H₅SiCl₃ in 60 ml of benzene.

The initial reaction is carried out at 16°C according to Example 1 and the mixture is subsequently heated at 55°C for about 15 hours. The product mixture obtained is first passed through a filter to remove the pyridine hydrochloride which forms. Next the benzene phase filtrate is stirred for one hour with 300 ml of water to hydrolyze the Si-Cl bonds to SiOH bonds on the intermediate compound C₆H₅ClSi[OSi(OC₄H₉sec.)₃]₂ molecules in the product mixture. Next the product mixture is washed with water until substantially Cl⁻ free and is then dried over CaCl₂ and MgSO₄ for 5 hours. The mixture is then filtered and vacuum stripped to yield a crude product mixture of about 153 grams.

Fractionation of the crude product mixture yields 113.2 grams (73.9% yield) of an alkoxysilanol cluster compound having the formula C₆H₅Si[OSi(OC₄H₉sec.)₃]₂OH. The compound is found to have a boiling point of about 164°C ±1.5° at a vacuum of about 0.05 to 0.07 mm Hg. The compound has the generic formula of C₃₀H₆₀O₉Si₃; calculated C—55.5%; H—9.3%; Si—12.98%; found C—55.51%; H—9.4%; and Si—12.99%. The OH group is confirmed by IR analysis.

EXAMPLE 5

The procedure of Example 1 is repeated except that the following constituents and amounts are used:
104.14 grams (0.394 moles) of HOSi(OC₄H₉sec.)₃;
43.6 grams (0.55 moles) of pyridine in 400 ml of benzene;
21.2 grams (0.132 moles) of C₂H₃SiCl₃ in 80 ml of benzene.

The initial reaction is carried out at about 6°C for about ½ hour and then the reaction mixture is heated to 55°C and maintained at that temperature for about 12 hours. The recovery and hydrolysis procedure of Example 1 is repeated and a mid-range fraction boiling at about 157°C ±1.5°C at 0.02 mm Hg is found to contain 41.4 grams of a compound having the formula C₂H₃Si[OSi(OC₄H₉sec.)₃]₂OH. Calculated values of substituents are C—52.13%; H—9.76%; and Si—14.07%; found C—51.9%; H—9.79%; and Si—13.6%. A high boiling point fraction is taken off at 197°C ±2° at 0.02 mm Hg. This high boiling fraction contains 13.4 grams of an alkoxysilanol cluster compound of the present invention having the formula C₂H₃Si[OSi(OC₄H₉sec.)₃]₃. Calculated C—53.99 %; H—10.01%; and Si—13.29%; found C—53.31%; H—10.02%; and Si—13.6%.

The products obtained from the above examples are tested for viscosity, wear scar and hydrolysis solids as shown in the following table. The ASTM slope based on viscosity measurements at 100°F and 210°F are calculated and used as an indication of change in viscosity in response to temperature changes. The wear scar test is performed with a four ball 40 kg load apparatus at 1800 rpm and 168°F for 1 hour. The hydrolysis solids test is carried out at 210°F in the presence of ⅓ weight H₂O and copper metal catalyst for 100 hours. The results establish that the compounds of the present invention are very good functional fluids, as follows:

TABLE

Physical Properties

| Compound tested: | Viscosity (centistokes) −40°F | 100°F | 210°F | ASTM Slope | Wear Scar (mm) | % Solids After Hydrolysis |
|---|---|---|---|---|---|---|
| [(sec.C₄H₉O)₃SiO]₂SiC₂H₅ \| OH | 750 | 10.12 | 2.76 | 0.85 | 0.92 | 0.12 |
| [(sec.C₄H₉O)₃SiO]₂Si—CH₃ \| OH | 399 | 15.67 | 4.82 | 0.55 | 0.79 | 0.08 |
| [(sec.C₄H₉O)₃SiO]₂Si—C₆H₅ \| OH | 4095 | 21.12 | 3.71 | 0.81 | 0.92 | 0.03 |
| [(sec.C₄H₉O)₃SiO]₂Si—CH=CH₂ \| OH | 376.1 | 10.86 | 3.24 | 0.64 | 0.76 | 0.05 |

What is claimed is:

1. A compound of the formula:

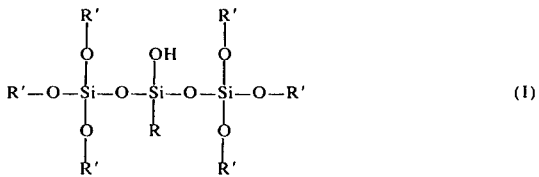

(1)

wherein R is hydrogen, an alkyl, alkenyl, aryl or aralkyl, and each R' is independently selected from the same group as R with the proviso that at least a majority of R' radicals are sterically hindered alkyl groups having at least 3 carbon atoms.

2. The compound of claim 1 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

3. The compound of claim 2 wherein a majority of the R' radicals are sterically hindered alkyl groups having about 3 to about 24 carbon atoms.

4. The compound of claim 1 wherein R is hydrogen, an alkyl having about 1 to about 8 carbon atoms or an aryl or aralkyl having about 6 to about 14 carbon atoms and wherein each R' is independently selected from the same group as R, subject to the above proviso.

5. The compound of claim 4 wherein a majority of the R' radicals are sterically hindered alkyl groups having about 4 to about 12 carbon atoms.

6. The compound of claim 1 wherein a majority of the R' radicals are sterically hindered alkyl groups having about 3 to about 24 carbon atoms.

7. The compound of claim 6 wherein a majority of the R' radicals are sterically hindered alkyl groups having about 4 to about 12 carbon atoms.

8. A method of preparing the compound of claim 1 comprising:

a. reacting a trihalosilane of the formula:

R-SiX$_3$ wherein R is defined in claim 1 above and each X is a halogen selected from F, Cl, Br and I; with about 1.5 to about 4 moles of a trialkoxysilanol per mole of trihalosilane, said trialkoxysilanol having the formula:

HOSi(OR')$_3$ wherein R' is defined in claim 1 above; in the presence of about 1.5 to about 4 moles of a hydrogen halide acceptor base compound, per mole of trihalosilane; to produce a reaction mixture containing an intermediate compound having the formula:

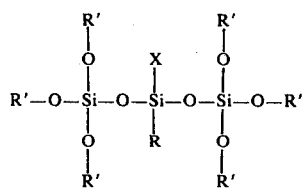

wherein all of the substituents are defined above; and b. subsequently reacting the intermediate compound with at least about 0.8 moles of water per mole of said intermediate compound to hydrolyze said intermediate compound to the compound of claim 1;

said reactions being carried out at about −30°C to about the reflux temperature of the lowest boiling constituent in the reaction mixture.

9. The method of claim 8 wherein X is selected from Cl, Br and I.

10. The method of claim 8 wherein R is hydrogen, an alkyl or alkenyl having about 1 to about 18 carbon atoms or an aryl or aralkyl having about 6 to about 24 carbon atoms and wherein each R' is independently selected from the same group as R with the proviso that at least a majority of the R' radicals are sterically hindered alkyl groups having about 3 to about 24 carbon atoms.

11. The method of claim 10 wherein R is hydrogen, an alkyl having about 1 to about 8 carbon atoms or an aryl or aralkyl having about 6 to about 14 carbon atoms and wherein each R' is independently selected from the same group as R, subject to the above proviso.

12. The method of claim 10 wherein a majority of the R' radicals are sterically hindered alkyl groups having about 4 to about 12 carbon atoms and wherein X is Cl.

13. The method of claim 10 wherein about 3 to about 6 moles of the trialkoxysilanol is used per mole of trihalosilane.

14. The method of claim 13 wherein about 3 to about 6 moles of the hydrogen halide acceptor base compound is used per mole of trihalosilane.

15. The method of claim 14 wherein said reaction is carried out at 0°C to 100°C.

* * * * *